US005998465A

United States Patent [19]
Hellberg et al.

[11] Patent Number: 5,998,465
[45] Date of Patent: Dec. 7, 1999

[54] ESTERS OF NON-STEROIDAL ANTI-FLAMMATORY CARBOXYLIC ACIDS

[75] Inventors: Mark Hellberg, Arlington; Pete Delgado, Fort Worth; Jon C. Nixon, Mansfield, all of Tex.

[73] Assignee: Alcon Laboratories, Inc., Fort Worth, Tex.

[21] Appl. No.: 09/139,506

[22] Filed: Aug. 25, 1998

Related U.S. Application Data

[62] Division of application No. 09/023,385, Feb. 13, 1998, which is a division of application No. 08/526,913, Sep. 12, 1995, Pat. No. 5,750,564.

[51] Int. Cl.$^6$ .......................... A01N 43/18; A01N 43/12; C07D 335/04; C07D 335/52
[52] U.S. Cl. .......................... 514/432; 514/443; 549/23; 549/49; 549/58
[58] Field of Search .................................. 514/432, 443; 549/23, 49, 58

[56] References Cited

U.S. PATENT DOCUMENTS

| | | | |
|---|---|---|---|
| 4,523,024 | 6/1985 | Shiono et al. | 549/407 |
| 4,550,022 | 10/1985 | Garabedian et al. | 424/606 |
| 4,681,890 | 7/1987 | Kanehira et al. | 514/333 |
| 4,857,516 | 8/1989 | Terao et al. | 514/100 |
| 4,975,419 | 12/1990 | Newton et al. | 514/6 |
| 4,988,728 | 1/1991 | Gerson et al. | 514/448 |
| 5,084,575 | 1/1992 | Kreft, III et al. | 546/174 |
| 5,424,321 | 6/1995 | Hellberg et al. | 546/337 |
| 5,750,564 | 5/1998 | Hellberg et al. | 514/469 |

FOREIGN PATENT DOCUMENTS

| | | |
|---|---|---|
| 0 183 869 A1 | 6/1986 | European Pat. Off. . |
| 0 345 593 | 12/1989 | European Pat. Off. . |
| 0 387 771 | 9/1990 | European Pat. Off. . |
| 0 525 360 A2 | 1/1993 | European Pat. Off. . |
| 0 527 458 A1 | 2/1993 | European Pat. Off. . |
| 0 640 609 A1 | 3/1995 | European Pat. Off. . |
| 0 645 383 A1 | 3/1995 | European Pat. Off. . |
| 0 719 760 A1 | 7/1996 | European Pat. Off. . |
| 3407 507 A1 | 9/1985 | Germany . |
| 58-072579 | 4/1983 | Japan . |
| 64-40484 A2 | of 1989 | Japan . |
| WO 96/20187 | 7/1996 | WIPO . |

OTHER PUBLICATIONS

Bazan, H.; "Response of Inflammatory Lipid Mediators following Corneal Injury"; *Lipid Mediators in Eye Inflammation New Trends Lipid Mediator Res. Basel*; Karger vol. 5; pp. 1–11 (1990).

Bellavite, P.; "The Superoxide–Forming Enzymatic System of Phagocytes"; *Free Radical Biology & Medicine;* 4; pp. 255–261 (1988).

Bonne, et al.; "2–(2–Hydroxy–4–methylphenyl)aminothiazole Hydrochloride as a Dual Inhibitor of Cyclooxygenase/Lipoxygenzse and a Free Radical Scavenger"; *Drug Research 39 II,* No. 10; pp. 1242–1245 (1989).

Campbell, W.; "Lipid–Derived Autacoids"; *Goodman and Gilman's The Pharmacological Basis of Therapeutics*, Pergman Press, New York; pp. 600–617 (1990).

Chow, C.; "Vitamin E and Oxidative Stress"; *Free Radical Biology & Medicine;* vol. 11; pp. 215–232 (1991).

Cohen, et al.; "Lewis Acid Mediated Nucleophilic Substitution Reactions"; *Journal of Organic Chemistry;* vol. 54; pp. 3282–3292 (1989).

Derwent Publications Ltd., London, GB; AN 83–55213k, "Indomethacin alpha–tocopherol ester preparation—by reacting indomethacin and alpha–tocopherol in and inert solvent" (JP 58072579 abstract), 1983.

Derwent Publications Ltd., AN 84–007991, 1984.
Derwent Publications Ltd., AN 85–027830, 1985.
Derwent Publications Ltd., AN 87–246978, 1987.
Derwent Publications Ltd., AN 930297401, 1993.

Duchstein and Gurka; "Activated Species of Oxygen: A challenge to Modern Pharmaceutical Chemistry"; *Archives of Pharmacology;* vol. 325; pp. 129–146 (1992).

Duniec, et al.; "Antioxidant properties of some chemicals vs their influence on cyclooxygenase and lipoxidase activities"; *Biochemical Pharmacology;* vol. 32; No. 14; pp. 2283–2286 (1983).

Gifford, H.; "The Treatment of Sympathetic Ophthalmia"; *Ophthalmoscope;* vol. 8; pp. 257–259 (1910).

Goa and Chrisp; "Ocular Diclofenac"; *Drugs & Aging;* vol. 2; No. 6; pp. 473–486 (1992).

Graff and Anderson; "1–[4–[3[[BIS(4–Flurorphenyl)hydroxymethyl]–1–peperidinyl]propoxy]–3–methoxyphenyl]ethanone (AHR–5333): A Selective Human Blood Neutrophil 5–Lipoxygenase Inhibitor"; *Prostaglandins;* vol. 38; No. 4; pp. 473–497 (1989).

Hammond et al. "Antioxidant–based inhibitors of leukotriene biosynthesis. The discovery of 6–[1–[2–(hydroxymethyl)phenyl]–1–propen–3–yl]–2, 3–dihydro–5–benzofuranol, a potent topical antiinflammatory agent", *Journal of Medicinal Chemistry,* vol. 33, No. 3, pp. 908–918 (1990).

Insel, P.; "Analgesic–Antipyretics and Antiinflammatory Agents"; *Goodman and Gilman's The Pharmacological Basis of Therpeutics*; Pergman Press, New York; pp. 638–669, 681 (1990).

Lamba, et al.; "Spectroscopic detection of lipid peroxidation products and structural changes in a sphingomyelin model system"; *Biochimica et Biophysica Acta;* vol. 1081; pp. 181–187 (1991).

(List continued on next page.)

*Primary Examiner*—D. Margaret Mach
*Attorney, Agent, or Firm*—Michael C. Mayo

[57] ABSTRACT

Compounds having anti-inflammatory and anti-oxidant activity are disclosed. The compounds are useful in preventing and treating inflammatory disorders through several mechanisms. Methods of treatment employing these properties of the compounds and corresponding pharmaceutical compositions are disclosed.

30 Claims, No Drawings

OTHER PUBLICATIONS

Nelson, P.; "Cyclooxygenase Inhibitors"; CRC Handbook of Eicosanoids: Prostaglandins, and Related Lipids, vol. II Drugs Acting Via the Eicosanoids; CRC Press, Boca Raton, FL; pp. 59–133 (1989).

Petty, et al.; "Protective effects of an α–tocopherol analogue against myocardial reperfusion injury in rats"; *European Journal of Pharmacology;* vol. 210; pp. 85–90 (1992).

Sies and Murphy, "Role of tocopherols in the protection of biological systems against oxidative damage"; *Journal of Photochemistry and Photobiology;* vol. 8; pp. 211–218 (1991).

Skoog and Beck; "Studies on the Fibrinogen, Dextran and Phytohemagglutinin Methods of Isolating Leukocytes"; *Blood;* vol. 11; pp. 436–454 (1956).

Vane, J.; "Inflammation and the mechanism of action of anti–inflammatory drugs"; *FASEB Journal;* vol. 1, pp. 89–96 (1987).

ESTERS OF NON-STEROIDAL ANTI-FLAMMATORY CARBOXYLIC ACIDS

This application is a divisional of U.S. patent application Ser. No. 09/023,385 filed Feb. 13, 1998; which is a divisional of U.S. patent application Ser. No. 08/526,913 filed Sep. 12, 1995, now U.S. Pat. No. 5,750,564.

BACKGROUND OF THE INVENTION

The present invention is directed to the provision of compounds having potent anti-inflammatory and anti-oxidant activity. The invention is further directed to compositions containing the compounds of the present invention for use in pharmaceutical applications. The invention is also directed to methods of using the compounds and compositions of the present invention to prevent and treat inflammatory disorders including ocular inflammation associated with ophthalmic disease and ophthalmic surgery.

Inflammation from cellular stress can cause excessive tissue damage. Numerous biochemical pathways are known to lead to inflammation. In general, the cyclooxygenase system produces prostaglandins, while the lipoxygenase system produces leukotrienes, "HETEs" and "HPETEs." Such agents have been associated with inflammation. See generally, *Goodman and Gilman's The Pharmacological Basis of Therapeutics*, pages 600–617, Pergman Press, NY (1990). Therapies designed to inhibit the production of these types of agents are therefore of great interest.

Non-steroidal anti-inflammatory agents (NSAIA) have been used for the treatment of inflammatory disorders. The following references may be referred to for further background concerning this use of NSAIAs:

*Ophthalmoscope,* volume 8, page 257 (1910);

*FASEB Journal,* volume 1, page 89 (1987); and

*Inflammation and Mechanisms and Actions of Traditional Drugs,* vol. I Anti-inflammatory and Anti-rheumatic drugs. Boca Raton, Fla., CRC Press, (1985).

However, there are some problems associated with NSAIA treatment including delivery to the appropriate site of action and side effects (*Goodman and Gilman's The Pharmacological Basis of Therapeutics,* pages 638–669, Pergman Press, NY (1990)).

Free radical molecules also play a major role in inflammation. These unstable chemical moieties lead to the oxidation of tissue resulting in damage. Such oxidative stress and damage has been described in *Biochemical Pharmacology,* 32(14), pages 2283–2286 (1983) and *Free Radicals in Biology and Medicine,* 4, pages 225–261 (1988). Agents that act as anti-oxidants can protect against oxidative damage. Such protection has been the subject of numerous scientific publications, including the following:

*Archives of Pharmacology,* volume 325, pages 129–146 (1992);

*Journal of Photochemistry and Photobiology,* volume 8, pages 211–224 (1991);

*Free Radicals in Biology and Medicine,* volume 11, pages 215–232 (1991); and

*European Journal of Pharmacology,* volume 210, pages 85–90 (1992).

The combination of anti-oxidant activity with other pharmacologically significant activities in a single molecule is discussed in JP 64-40484 and EP 387771 A2; and compounds with cyclooxygenase/5-Lipoxygenase and anti-oxidant activity are discussed in *Drug Research,* 39(II) Number 10, pages 1242–1250 (1989). However, these references do not disclose the compounds of the present invention.

The present invention is directed to the provision of new compounds that have both potent anti-inflammatory activity and potent anti-oxidant activity in a single molecule. The use of a single chemical entity with potent anti-inflammatory and potent anti-oxidant activity provides increased protection relative to the use of a compound with singular activity. The use of a single agent having both activities over a combination of two different agents provides uniform delivery of an active molecule, thereby simplifying issues of drug metabolism, toxicity and delivery.

SUMMARY OF INVENTION

The present invention provides new compounds having potent anti-inflammatory and anti-oxidant activity. The dual therapeutic efficacies act in a complementary manner to reduce cellular damage. Additionally, the compounds of the present invention exhibit 5-lipoxygenase inhibitory activity not present in the individual agents.

The compounds of the present invention are useful as cytoprotective agents. These compounds include a non-steroidal anti-inflammatory agent (NSAIA) moiety and an anti-oxidant moiety. In order to provide effective therapy for inflammatory disorders, the present invention takes advantage of these individual efficacies. In addition, the present invention improves upon these individual efficacies by providing greater drug delivery to the target tissues by means of administering a single drug having multiple therapeutic actions. Finally, the compounds of the present invention exhibit therapeutic properties which are not present in the individual moieties of the compounds. These and other advantages of the present invention will be apparent to those skilled in the art based on the following description.

The NSAIA component of the compounds provides anti-inflammatory activity. The use of these NSAIAs will provide inhibition of cyclooxygenase, an important enzyme involved in the prostaglandin/inflammation pathway. The compounds also include an anti-oxidant component. As oxidative stress has been implicated in inflammatory responses, the presence of an anti-oxidant will further help treat the target tissue.

The compounds of the present invention also exhibit properties present only in the combined molecule, not in the individual components. One such property is the inhibitory efficacy against 5-lipoxygenase, an enzyme known to be involved in inflammation.

Another advantage of the present invention is that the anti-inflammatory moiety and the anti-oxidant moiety are linked through an ester bond. Since the carboxylic acid moiety of the NSAIA has been converted to an ester, the resultant molecule is neutrally charged, thus increasing lipophilicity and drug delivery. Furthermore, the esters, acting as pro-drugs, can move to the site of inflammation, where esterases, present as tissue constituents or released as part of the inflammatory response, will catalyze the hydrolysis of the ester and release the non-steroidal anti-inflammatory agent and anti-oxidant.

The compounds of the present invention are capable of protecting against cellular damage by a wide range of insults. Since the compounds provide this protection by decreasing free radical or oxidative damage, reducing cyclooxygenase or lipoxygenase mediated inflammation, and improving site delivery, this therapy represents an improved two-pronged approach to cytoprotection.

DETAILED DESCRIPTION OF INVENTION

The compounds of the present invention are of the formula (I) or (II):

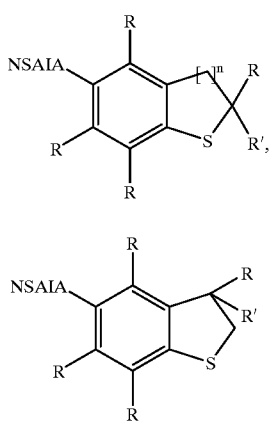

(I)

(II)

wherein:
NSAIA is a non-steroidal anti-inflammatory agent containing a carboxylic acid, and is attached through the acid to form a phenolic ester;
R is $C_1$–$C_3$ alkyl;
R' is $(CH_2)_m X'$;
m is 1 to 6;
X' is OH, OR, $NH_2$, NHR or H;
n is 1 to 2; and
X is O, S or NC(O)R.

The compounds of the present invention also include pharmaceutically acceptable salts of the compounds of formulas (I) and (II).

The compounds of the present invention contain a non-steroidal anti-inflammatory agent (NSAIA) having a carboxylic moiety. A number of chemical classes of non-steroidal anti-inflammatory agents have been identified. The following text, the entire contents of which are hereby incorporated by reference in the present specification, may be referred to for various NSAIA chemical classes: *CRC Handbook of Eicosanoids: Prostaglandins, and Related Lipids, Volume II, Drugs Acting Via the Eicosanoids*, pages 59–133, CRC Press, Boca Raton, Fla. (1989). The NSAIA may be selected, therefore, from a variety of chemical classes including, but not limited to, fenamic acids, such as flufenamic acid, niflumic acid and mefenamic acid; indoles, such as indomethacin, sulindac and tolmetin; phenylalkanoic acids, such as suprofen, ketorolac, flurbiprofen and ibuprofen; and phenylacetic acids, such as diclofenac. Further examples of NSAIAs are listed below:

| loxoprofen | tolfenamic acid | indoprofen |
| pirprofen | clidanac | fenoprofen |
| naproxen | fenclorac | meclofenamate |
| benoxaprofen | carprofen | isofezolac |
| aceloferac | fenbufen | etodolic acid |
| fleclozic acid | amfenac | efenamic acid |
| bromfenac | ketoprofen | fencloenac |
| alcofenac | orpanoxin | zomopirac |
| diflunisal | pranoprofen | zaltoprofen |

The preferred compounds are those wherein the NSAIA is selected from naproxen, flurbiprofen or diclofenac. The most preferred compounds are those wherein the NSAIA is selected from naproxen or flurbiprofen.

With respect to the other substituents of the compounds of formulas (I) and (II), the preferred compounds are those wherein:

R is $CH_3$;
m is 1 to 2;
X' is H or OH; and
X is O.

The following compounds are particularly preferred:

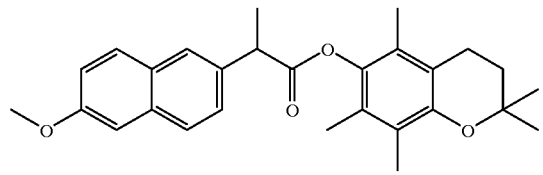

6-(2,2,5,7,8-pentamethyl-3,4-dihydro-2H-benzo[1,2b]pyran) 2-(6-methoxy-2-naphthyl)-propionate ("Compound A");

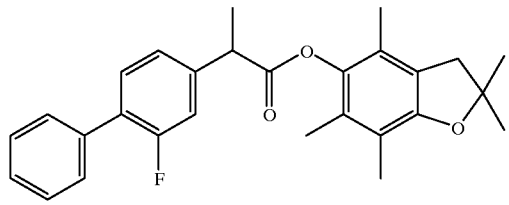

5-(2,2,4,6,7-pentamethyl-2,3-dihydro-benzo[1,2-b]furan) 2-(3-fluoro-4-phenyl-phenyl)-propionate ("Compound B");

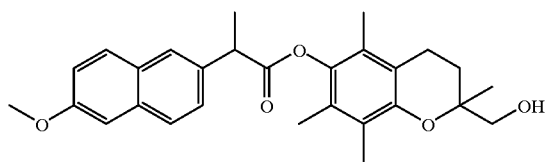

6-(2-hydroxymethyl-2,5,7,8-tetramethyl-3,4-dihydro-2H-benzo[1,2-b]pyran) 2-(6-methoxy-2-naphthyl)-propionate ("Compound C");

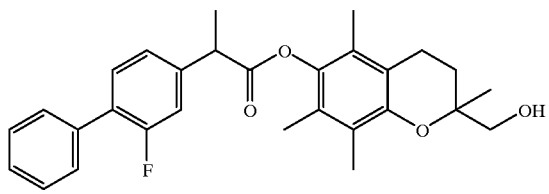

6-(2-hydroxymethyl-2,5,7,8-tetramethyl-3,4-dihydro-2H-benzo[1,2-b]pyran) 2-(3-fluoro-4-phenyl-phenyl)-propionate ("Compound D"); and

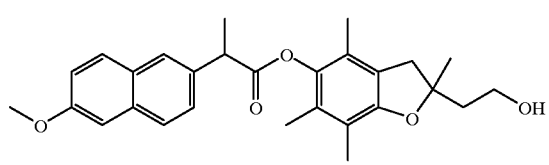

5-(2-(2-hydroxyethyl)-2,4,6,7-tetramethyl-2,3-dihydro-benzo[1,2-b]furan) 2-(6-methoxy-2-naphthyl)-propionate ("Compound E").

The compounds of the present invention may be prepared by the methods illustrated in Scheme I below:

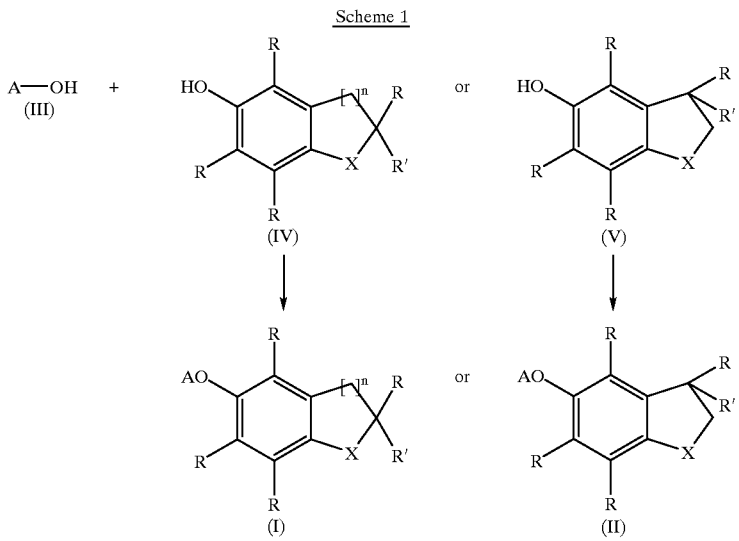

The NSAIAs containing a carboxylic acid (III) are reacted with the appropriate phenol derivative, (IV) or (V), in the presence of a coupling reagent, such as dicyclohexylcarbodiimide or 1-(3-dimethylaminopropy)-3-ethyl carbodiimide HCl, and 4-dimethylamino pyridine or 1-hydroxybenzotriazole, in an inert organic solvent, such as acetonitrile or tetrahydrofuran, and at a temperature from 0 to 500C. The use of certain protecting groups and deprotection steps may be necessary, as will be appreciated by those skilled in the art.

Compounds of formulas (I) and (II) may exist as mixtures of stereoisomers. The preparation of the individual stereoisomer may be performed by preparing and resolving the carboxylic acid, (III), by known methods, and then using a single stereoisomer for subsequent reactions. The resulting diastereomeric esters (I) or (II) may then be separated using repeated re-crystallization or by chromatographic techniques.

Methods of synthesizing the compounds of formulas (I) and (II) are further illustrated by the following examples:

EXAMPLE 1
Synthesis of 6-(2,2,5,7,8-pentamethyl-3,4-dihydro-2H-benzo[1,2-b]pyran) 2-(6-methoxy-2-naphthyl)-propionate (Compound A)

A solution of 6-hydroxy-2,2,5,7,8-pentylmethyl-3,4-dihydro-2H-benzo[1,2-b]pyran (*Journal of Organic Chemistry*, volume 30, pages 311–317, (1939), 1.2 g, 5.51 mmol) and 6-methoxy-a-methyl-2-napthaleneacetic acid (Aldrich, 1.39 g, 6.06 mmol) is stirred in the presence of 4-dimethylamino-pyridine (Aldrich, 0.67 g, 5.51 mmol) and 1-(3-dimethylaminopropyl)-3-ethyl-carbodiimide hydrochloride (Aldrich, 1.06 g, 5.51 mmol) in tetrahydrofuran (25 mL). The reaction mixture is stirred at ambient temperature under nitrogen for 24 hours. The solution is diluted with ethyl acetate (150 mL), washed with water, dried (sodium sulfate) and concentrated under reduced pressure. The residue is purified by standard methods to give 6-(2,2,5,7,8-pentamethyl-3,4-dihydro-2H-benzo[1,2-b]pyran) 2-(6-methoxy-2-naphthyl)-propionate.

EXAMPLE 2
Synthesis of 5-(2,2,4,6,7-pentamethyl-2,3-dihydro-benzo[1,2-b]furan) 2-(3-fluoro-4-phenyl-phenyl)-propionate (Compound B)

A solution of 5-hydroxy-2,2,4,6,7-pentamethyl-2,3-dihydro-benzo[1,2-b]furan (*Journal of Organic Chemistry*, volume 58, pages 7421–26, (1993), 1.13 g, 5.51 mmol) and 2-(3-fluoro-4-phenyl-phenyl)-propionate (Sigma, 1.48 g, 6.06 mmol) is stirred in the presence of 4-dimethylamino pyridine (Aldrich, 0.67 g, 5.51 mmol) and 1-(3-dimethylaminopropyl)-3-ethyl-carbodiimde hydrochloride (Aldrich, 1.06 g, 5.51 mmol) in tetrahrdofuran (25 mL). The reaction mixture is stirred at ambient temperature under nitrogen for 24 hours. The solution is diluted with ethyl acetate (150 mL), washed with water, dried (sodium sulfate) and concentrated under reduced pressure. The residue is purified using standard methods to give 5-(2,2,4,6,7-pentamethyl-2,3-dihydro-benzo[1,2-b]furan) 2-(3-fluoro-4-phenyl-phenyl)-propionate.

EXAMPLE 3
Synthesis of 6-(2-hydroxymethyl-2,5,7,8-tetramethyl-3,4-dihydro-2H-benzo[1,2-b]pyran) 2-(6-methoxy-2-naphthyl)-propionate (Compound C)

The title compound was prepared by a multiple step synthesis. The intermediate 2-(t-butyldimethylsilyloxymethyl)-6-hydroxy-2,5,7,8-tetratmethyl-3,4-dihydro -2H-benzo[1,2-b]pyran, was first synthesized:

A solution of 6-hydroxy,-2-hydroxymethyl-2,5,7,8-tetramethyl-3,4-dihyro-2H-benzo[1,2-b]pyran, (3.14 g, 46.1 mmol), prepared by the reduction of the commercially available acid (Aldrich) using lithium aluminum hydride, and t-butyldimethylsilyl chloride (3.06 g, 20.3 mmol) in dimethylformamide (10 mL) was stirred at room temperature for 23 hours. The reaction mixture was diluted with water (200 mL) and the product extracted with ethyl acetate (4×50 mL). The combined organic extracts were dried over sodium sulfate, and concentrated under reduced pressure. The residue was purified by column chromatography on silica gel with a gradient elution of hexane/ethyl acetate to give 5.38 g (83.8% yield) of 2-(t-butyldimethylsilyloxymethyl)-6-hydroxy-2,5,7,8-tetratmethyl-3,4-dihydro-2H-benzo[1,2-b]pyran as an oil.

$^1$H-NMR (CDCl$_3$) in ppm: 0.034 (s,3H), 0.0955(s,3H), 0.897 (s,9H), 1.231 (s,3H), 1.650–2.050 (m,2H), 2.097 (s,3H), 2.113 (s,3H), 2.154 (s,3H), 2.601 (t,2H), 3.516–3.577 (q,2H), 4.152 (2,1H)

The intermediate 2-(t-butyldimethylsilyloxymethyl)-6-hydroxy-2,5,7,8-tetrethyl-3,4-dihydro-2H-benzo[1,2-b]pyran was then coupled to provide the intermediate 6-(2-(t-butyldimethylsilyloxymethyl)-2,5,7,8-tetratmethyl-3,4-dihydro -2H-benzo[1,2-b]pyran) 6-methoxy-2-naphthyl)-propionate:

A solution of 2-(t-butyldimethylsilyloxymethyl)-6-hydroxy-2,5,7,8-tetramethyl-3,4-dihydro-2H-benzo[1,2-b]pyran (1.34 g, 3.83 mmol), 6-methoxy-a-methyl-2-napthaleneacetic acid 0.92 g, 4.21 mmol) 4-dimethylaminopyridine (0.51, 4.21 mmol) and 1-(3-dimethylaminopropyl)-3-ethyl-carbodiimde (0.81 g, 4.21 mmol), in tetrahydrofuran (15 mL) was stirred at room temperature for 72 hours. The reaction mixture was diluted with ethyl acetate (200 mL), washed with diluted hydrochloric acid (3%, 2×50 mL), brine (2×50 mL) and dried over sodium sulfate. The mixture was concentrated under reduced pressure to give 1.98 g (91.7% yield) of 6-(2-(t-butyldimethylsilyloxymethyl)-2,5,7,8-tetramethyl-3,4-dihydro-2H-benzo[1,2-b]pyran) 2-(6-methoxy-2-naphthyl)-propionate as a light tan oil which was used without further purification.
(2-hydroxymethyl-2,5,7,8-tetramethyl-3,4-dihydro-2H-benzo[1,2-b]pyran) 2-(6-methoxy-2-naphthyl)-propionate (Compound C):

A solution tetrabutyl ammonium fluoride (1M in tetrahydrofuran, 3.5 mL, 3.5 mmol) was added to a solution of 6-(2-(t-butyldimethylsilyloxymethyl)-2,5,7,8-tetramethyl-3,4-dihydro-2H-benzo[1,2-b]pyran) 2-(6-methoxy-2-naphthyl)-propionate (1.98 g, 3.52 mmol) in tetrahydrofuran (15 mL). The reaction mixture was stirred at ambient temperature for 2 hours, diluted with water (100 mL) and the product extracted with ethyl acetate (3×75 mL). The pH of the aqueous layer was adjusted to pH 5 with 1 N hydrochloric acid and the resulting solution was extracted with ethyl acetate (50 mL). The combined organic extracts were dried over sodium sulfate and concentrated under reduced pressure. The residue was purified by column chromatography on silica gel with a gradient elution of hexane/ethyl acetate to give 0.96 g of an oil. Crystallization from ethyl ether/hexane afforded 0.76 g (44.1% yield) of a white solid. Melting point 114–116° C. Elemental Analysis: calculated for C-74.98, H-7.19; found C-74.89, H-7.22.
$^1$H-NMR (CDCl$_3$) in ppm: 1.194 (2,3H), 1.573–2.180 (m,15H), 2.590 (br s,2H), 3.594 (m,2H), 3.929 (s,3H), 4.110–4.230 (q,1H), 7.136–7.175 (m,2H), 7.550–7.584 (d,2H), 7.723–7.817 (m,2H)

EXAMPLE 4

6-(2-hydroxymethyl-2,5,7,8-tetramethyl-3,4-2H-benzo[1,2-b]pyran) 2-(3-flouro-4-phenyl-phenyl)-propionate (Compound D)

Following the procedure of example 3, the title compound is prepared by substituting 2-(3-fluoro-4-phenyl-phenyl)-propionate for 6-methoxy-a-methyl-2-napthaleneacetic acid.

EXAMPLE 5

5-(2-(2-hydroxyethyl)-2,4,6,7-tetramethyl-2,3-dihydro-benzo[1,2-b]furan) 2-(6-methoxy-2-napthyl)-propionate (Compound E)

A solution of 2-(5-hydroxy-2,4,6,7-tetramethyl-2,3-dihydro-benzo[1,2-b]furan-2-yl) ethanol (*Journal of Heterocyclic Chemistry*, volume 30, pages 679–690 (1993), 1.30g, 5.51 mmol), 6-methoxy-a-methyl-2-napthaleneacetic acid (1.39, 6.06 mmol), 4-dimethylanimopyridine (0.67 g, 5.51 mmol) and 1-(3-dimethylaminopropyl)-3-ethyl-carbodiimide hydrochloride (1.06, 5.51 mmol) in tetrahydrofuran (25 mL) was stirred at ambient temperature under nitrogen for 24 hours. The reaction mixture was diluted with ethyl acetate (150 mL) and washed with water (2×40 mL) and brine (30 mL). The organic phase was separated, dried (sodium sulfate) and concentrated under reduced pressure. The residue was purified with column chromatography over silica gel, eluting with a gradient of ethyl acetate/hexane to give 1.84 g of a foam. Crystallization from methylene chloride/hexane followed by recrystallization from methylene/hexane afforded 0.32 (13% yield) of 5-(2-hydroxymethyl-2,4,6,7-tetramethyl-2,3-dihydro-benzo[1,2-b]furan) 2-(6-methoxy-2-napthyl)-propionate as a pale yellow solid. Melting point 94–95° C. Elemental Analysis: Calculated for C-74.89%, H-7.19%; found C-75.18, H-7.07.
$^1$H-NMR (CDCl$_3$): 1.328 (s,3H), 1.534–1.571 (d,3H), 1.962–2.031 (t,2H), 2.003 (s,3H), 2.050 (s,3H), 2.102 (s,3H), 2.671–2.748 (d,1H), 2.896–2.973 (d,1H), 3.751–3.868 (q,1H), 3.910 30 (s,3H), 4.234 (t,2H), 7.107–7.180 (m,2H), 7.345–7.401 (m,1H), 7.640–7.710 (m,2H).

The compounds of formulas (I) and (II) may be contained in various types of pharmaceutical compositions, in accordance with formulation techniques known to those skilled in the art. For example, the compounds may be included in tablets, capsules, solutions, suspensions and other dosage forms adapted for oral administration; solutions and suspensions adapted for parenteral use; solutions and suspensions adapted for intra-vitreal or intra-cameral use; and suppositories for rectal use. Solutions, suspensions and other dosage forms adapted for topical application to the involved tissues, such as tissue irrigating solutions, are particularly preferred for treatment of acute conditions associated with surgery or other forms of trauma.

The present invention is particularly directed to the provision of compositions adapted for treatment of ophthalmic tissues. The ophthalmic compositions of the present invention will include one or more compounds of formulas (I) and (II) and a pharmaceutically acceptable vehicle. Various types of vehicles may be used. The vehicles will generally be aqueous in nature. Aqueous solutions are generally preferred, based on ease of formulation, as well as a patient's ability to easily administer such compositions by means of instilling one to two drops of the solutions in the affected eyes. However, the compounds of formulas (I) and (II) may also be readily incorporated into other types of compositions, such as suspensions, viscous or semi-viscous gels or other types of solid or semi-solid compositions. Suspensions may be preferred for compounds of formulas (I) and (II) which are relatively insoluble in water. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% weight/volume ("% w/v").

Some of the compounds of formulas (I) and (II) may have limited solubility in water and therefore may require a surfactant or other appropriate co-solvent in the composition. Such co-solvents include: polyethoxylated castor oils, Polysorbate 20, 60 and 80; Pluronic® F-68, F-84 and P-103 (BASF Corp., Parsippany N.J., USA); cyclodextrin; or other agents known to those skilled in the art. Such co-solvents are typically employed at a level of from 0.01 to 2% w/v.

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxypropyl methylcellulose, hydroxyethyl cellulose, carboxymethyl cellulose, hydroxypropyl cellulose or other agents known to those skilled in the art. Such agents are typically employed at a level of from 0.01 to 2% w/v.

The route of administration (e.g., topical, parenteral or oral) and the dosage regimen will be determined by skilled clinicians, based on factors such as the exact nature of the condition being treated, the severity of the condition, the age and general physical condition of the patient, and so on.

As indicated above, use of the compounds of formulas (I)and (II) to prevent or reduce damage to ophthalmic tissues at the cellular level is a particularly important aspect of the present invention. Ophthalmic conditions which may be treated include, but are not limited to, cataracts, retinopathies, heredodegenerative diseases, macular degeneration, ocular ischemia, glaucoma, and damage associated with injuries to ophthalmic tissues, such as ischemia reperfusion injuries, photochemical injuries, and injuries associated with ocular surgery, particularly injuries to the retina, cornea or other tissues caused by exposure to light or surgical instruments. The compounds may also be used as an adjunct to ophthalmic surgery, such as by vitreal or subconjunctival injection following ophthalmic surgery. The compounds may be used for acute treatment of temporary conditions, or may be administered chronically, especially in the case of degenerative disease. The compounds may also be used prophylactically, especially prior to ocular surgery or noninvasive ophthalmic procedures, or other types of surgery.

The use of physiologically balanced irrigating solutions as pharmaceutical vehicles for the compounds of formulas (I) and (II) is preferred when the compositions are administered intraocularly. As used herein, the term "physiologically balanced irrigating solution" means a solution which is adapted to maintain the physical structure and function of tissues during invasive or noninvasive medical procedures. This type of solution will typically contain electrolytes, such as sodium, potassium, calcium, magnesium and/or chloride; an energy source, such as dextrose; and a buffer to maintain the pH of the solution at or near physiological levels. Various solutions of this type are known (e.g., Lactated Ringers Solution). BSS® Sterile Irrigating Solution and BSS Plus® Sterile Intraocular Irrigating Solution (Alcon Laboratories, Inc., Fort Worth, Tex., USA) are examples of physiologically balanced intraocular irrigating solutions. The latter type of solution is described in U.S. Pat. No. 4,550,022 (Garabedian, et al.), the entire contents of which are hereby incorporated in the present specification by reference.

The pharmaceutical compositions containing one or more compounds of formulas (I) and (II) may be used to treat patients afflicted with or prone to various types of cellular damage. In particular, these compositions may be used for inflammation and allergic diseases where prostaglandins and leukotrienes are known to participate. The concentrations of the compounds in the compositions will depend on various factors, including the nature of the condition to be treated with the compositions.

In general, the doses utilized for the above described purposes will vary, but will be in an effective amount to inhibit or reduce inflammation and/or oxidative tissue damage. As used herein, the term "pharmaceutically effective amount" refers to an amount of a compound of formulas (I) and (II) which will inhibit or reduce inflammation and/or oxidative tissue damage in a human patient. The doses utilized for any of the above-described purposes will generally be from about 0.01 to about 100 milligrams per kilogram of body weight (mg/kg), administered one to four times per day. When the compositions are dosed topically, they will generally be in a concentration range of from 0.001 to about 5% w/v, with 1–2 drops administered 1–4 times per day.

As used herein, the term "pharmaceutically acceptable carrier" refers to any formulation which is safe, and provides the appropriate delivery for the desired route of administration of an effective amount of at least one compound of the present invention. As such, all of the above-described formulations of the present invention, and all of following formulation examples of the present invention are hereby referred to as "pharmaceutically acceptable carriers."

The compositions of the present invention are further illustrated in the following formulation examples, compounds of the present invention are represented generically in some examples as "Compound."

Example 1

The following two-part formulation is similar to the BSS Plus® Intraocular Irrigating Solution available from Alcon Laboratories, Inc., Fort Worth, Tex., USA. That product, which is described in U.S. Pat. No. 4,550,022 (Garabedian, et al.), consists of two solutions referred to as "Part I" and "Part II," respectively. The following description illustrates how that product or similar products could be modified to incorporate the present invention.

Part I (basic solution) is made by dissolving sodium chloride, potassium chloride, and anhydrous dibasic sodium phosphate in water for injection at about 20° C. Then sodium bicarbonate is added and dissolved. Additional water for injection is added to make the desired volume and 1N HCl is added to adjust the pH to about 7.4. The solution is then passed through a 0.45 micron Millipore filter and placed in a bottle. The filled bottle is then stoppered, evacuated and sealed. The sealed bottle is sterilized by autoclaving at 121° C. for about 23 minutes.

Part II (acidic solution) is made by dissolving calcium chloride dihydrate, magnesium chloride hexahydrate, dextrose, and glutathione in water for injection. The solution is then sterile filtered through a 0.22 micron membrane filter and aseptically filled into a presterilized bottle and sealed with a presterilized rubber stopper. One or more of a compound of formula (I) or (II), for preventing or ameliorating inflammation and/or tissue oxidative damage, may be added to either the basic solution or the acidic solution, depending on the pKa of the compound of the present invention selected.

When Parts I and II are combined, the composition of the resulting formulation is as follows:

| Ingredients | Concentration millimolar (mM) |
| --- | --- |
| Oxidized Glutathione | 0.01–3.0 |
| Compound | 0.5–10.0% (weight/volume) |
| Bicarbonate | 1–50 |
| Calcium | 0.1–5 |
| Magnesium | 0.1–10 |
| Potassium | 1–10 |
| Sodium | 50–500 |
| Phosphate | 0.1–5 |
| Glucose | 1–25 |
| Chloride | 50–500 |
| Sodium Hydroxide and/or Hydrochloric Acid | Adjust pH |
| Water for Injection | q.s. |

The invention may also be embodied in products formulated or configured differently from the two-part product described above. For example, the acidic solution containing glutathione can be lyophilized (i.e., freeze-dried) following preparation and then reconstituted as a solution prior to use. That type of formulation is described in U.S. Pat. No. 4,975,419.

Example 2

Topical ophthalmic compositions useful for treating inflammation and/or tissue oxidative damage:

| Component | % w/v |
| --- | --- |
| Compound | 0.05–5.0 |
| Tyloxapol | 0.01–0.05 |
| HPMC | 0.5 |
| Benzalkonium Chloride | 0.01 |
| Sodium Chloride | 0.8 |
| Edetate Disodium | 0.01 |
| NaOH/HCl | q.s. pH 7.4 |
| Purified Water | q.s. 100 mL |

Example 3

A preferred topical ophthalmic composition useful for treating inflammation and/or tissue oxidative damage:

| Component | % w/v |
| --- | --- |
| Compound E | 0.10 |
| Tyloxapol | 0.01–0.05 |
| HPMC | 0.5 |
| Benzalkonium Chloride | 0.01 |
| Sodium Chloride | 0.8 |
| Edetate Disodium | 0.01 |
| NaOH/HCl | q.s. pH 7.4 |
| Purified Water | q.s. 100 mL |

The above formulation is prepared by first placing a portion of the purified water into a beaker and heating to 90° C. The hydroxypropylmethylcellulose (HPMC) is then added to the heated water and mixed by means of vigorous vortex stirring until all of the HPMC is dispersed. The resulting mixture is then allowed to cool while undergoing mixing in order to hydrate the HPMC. The resulting solution is then sterilized by means of autoclaving in a vessel having a liquid inlet and a hydrophobic, sterile air vent filter.

The sodium chloride and the edetate disodium are then added to a second portion of the purified water and dissolved. The benzalkonium chloride is then added to the solution, and the pH of the solution is adjusted to 7.4 with 0.1 M NaOH/HCl. The solution is then sterilized by means of filtration.

Compound E is sterilized by either dry heat or filtered. The sterilized anti-inflammatory agent is weighed aseptically and placed into a pressurized ballmill container. The tyloxapol, in sterilized aqueous solution form, is then added to the ballmill container. Sterilized glass balls are then added to the container and the contents of the container are milled aseptically at 225 rpm for 16 hours, or until all particles are in the range of approximately 5 microns.

Under aseptic conditions, the micronized drug suspension formed by means of the preceding step is then poured into the HPMC solution with mixing. The ballmill container and balls contained therein are then rinsed with a portion of the solution containing the sodium chloride, the edetate disodium and benzalkonium chloride. The rinse is then added aseptically to the HPMC solution. The final volume of the solution is then adjusted with purified water and, if necessary, the pH of the solution is adjusted to pH 7.4 with NaOH/HCl.

Example 4

Formulation for oral administration:

Tablet:

10–1000 mg of a Compound with inactive ingredients such as starch, lactose and magnesium stearate can be formulated according to procedures known to those skilled in the art of tablet formulation.

Example 5

Formulation for intraocular injection:

| Component | each mL contains: |
| --- | --- |
| Compound | 10–100 mg |
| Sodium Chloride | 7.14 mg |
| Potassium Chloride | 0.38 mg |
| Calcium chloride dihydrate | 0.154 mg |
| Magnesium chloride hexahydrate | 0.2 mg |
| Dried sodium phosphate | 0.42 mg |
| Sodium bicarbonate | 2.1 mg |
| Dextrose | 0.92 mg |
| Hydrochloride acid or sodium hydroxide | q.s., pH to approx. 7.2 |
| Water for injection | q.s. |

Example 6

A preferred formulation for oral administration:

Tablet:

5–100 mg of Compound E with inactive ingredients such as starch, lactose and magnesium stearate can be formulated according to procedures known to those skilled in the art of tablet formulation.

Example 7

A preferred bio-replacement formulation for intra-ocular administration:

| Ingredient | each mL contains: |
| --- | --- |
| Compound E | 0.01–1.0 (% w/v) |
| Sodium chondroitin sulfate | 40 mg |
| Sodium hyaluronate | 30 mg |
| Sodium dihydrogen phosphate hydrate | 0.45 mg |
| Disodium hydrogen phosphate | 2.00 mg |
| Sodium chloride | 4.3 mg |
| Purified water | q.s. |

What is claimed:

1. A compound of formula (I) or (II):

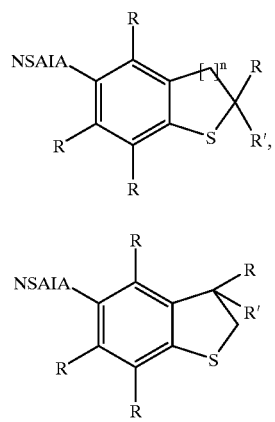

wherein:
NSAIA is a non-steroidal anti-inflammatory agent originally containing a carboxylic acid, and is attached through the acid to form a phenolic ester;
R is $C_1$–$C_3$ alkyl;
R' is $(CH_2)_m X'$;
m is 1 to 6;
X' is OH, OR, $NH_2$, NHR or H;
n is 1 to 2;
or a pharmaceutically acceptable salt thereof.

2. A compound according to claim 1, wherein:
R is $CH_3$;
m is 1 to 2; and
X' is H or OH.

3. A compound according to claim 1, wherein the NSAIA is selected from the group consisting of: fenamic acids; indoles; and phenylalkanoic acids.

4. A compound according to claim 3, wherein:
R is $CH_3$;
m is 1 to 2; and
X' is H or OH.

5. A compound according to claim 1, wherein the NSAIA is selected from the group consisting of:
loxoprofen; tolfenamic acid; indoprofen; pirprofen; clidanac; fenoprofen; naproxen; fenclorac; meclofenamate; benoxaprofen; carprofen; isofezolac; aceloferac; fenbufen; etodolic acid; fleclozic acid; amfenac; efenamic acid; bromfenac; ketoprofen; fenclofenac; alcofenac; orpanoxin; zomopirac; diflunisal; flufenamic acid; niflumic acid; mefenamic acid; pranoprofen; zaltoprofen; indomethacin; sulindac; tolmetin; suprofen; ketorolac; flurbiprofen; ibuprofen; and diclofenac.

6. A compound according to claim 5, wherein:
R is $CH_3$;
m is 1 to 2; and
X' is H or OH.

7. A compound according to claim 1, wherein the NSAIA is selected from the group consisting of naproxen, flurbiprofen and diclofenac.

8. A compound according to claim 7, wherein NSAIA is naproxen.

9. A compound according to claim 7, wherein NSAIA is flurbiprofen.

10. A compound according to claim 7, wherein NSAIA is diclofenac.

11. A compound according to claim 7, wherein:
R is $CH_3$;
m is 1 or 2; and
X' is H or OH.

12. A compound according to claim 11, wherein NSAIA is naproxen.

13. A compound according to claim 11, wherein NSAIA is flurbiprofen.

14. A compound according to claim 11, wherein NSAIA is diclofenac.

15. A compound according to claim 1, wherein the compound is selected from the group consisting of:

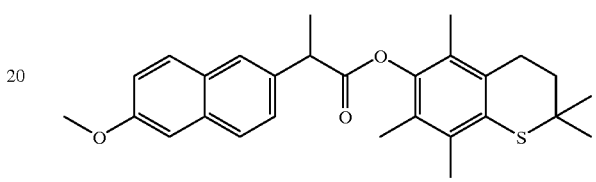

6-(1-acetyl-2,2,5,7,8-pentamethyl-3,4-dihydro-2H-benzothiin) 2-(6-methoxy-2-naphthyl)-propionate;

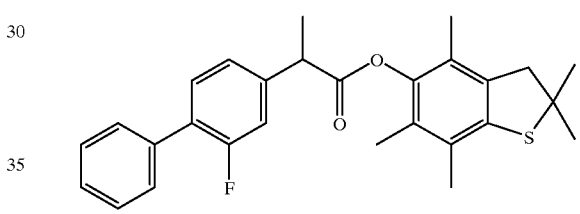

5-(1-acetyl-2,2,4,6,7-pentamethyl-2,3-dihydrobenzothiophene) 2-(3-fluoro-4-phenyl-phenyl)-propionate;

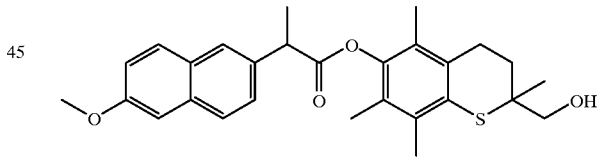

6-(1-acetyl-2-hydroxymethyl-2,5,7,8-tetramethyl-3,4-dihydro-2H-benzothiin) 2-(6-methoxy-2-naphthyl)-propionate;

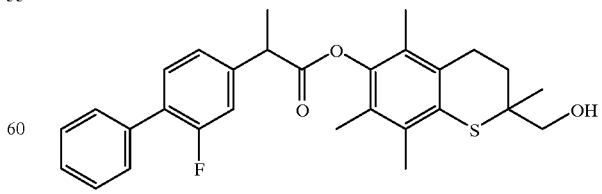

6-(1-acetyl-2-hydroxymethyl-2,5,7,8-tetramethyl-3,4-dihydro-2H-benzothiin) 2-(3-fluoro-4-phenyl-phenyl)-propionate; and

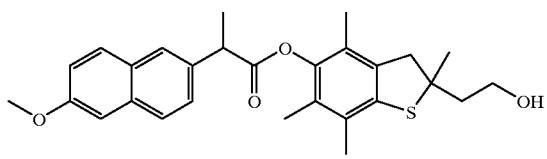

5-(1-acetyl-2-(2-hydroxyethyl)-2,4,6,7-tetramethyl-2,3-dihydrobenzothiophene) 2-(6-methoxy-2-naphthyl)-propionate.

16. A pharmaceutical composition for preventing or alleviating damage to mammalian tissues comprising an amount of a compound of formula (I) or (II) effective to decrease inflammation and free radical or oxidative damage in said tissues in a pharmaceutically acceptable vehicle:

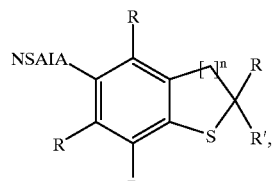

(I)

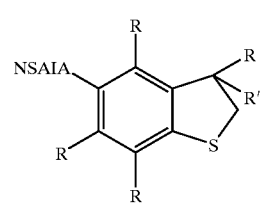

(II)

wherein:
NSAIA is a non-steroidal anti-inflammatory agent originally containing a carboxylic acid, and is attached through the acid to form a phenolic ester;
R is $C_1$–$C_3$ alkyl;
R' is $(CH_2)_m X'$;
m is 1 to 6;
X' is OH, OR, $NH_2$, NHR or H;
n is 1 to 2;
or a pharmaceutically acceptable salt thereof; and a pharmaceutically acceptable vehicle therefore.

17. A composition according to claim 16, wherein:
R is $CH_3$;
m is 1 to 2;
X' is H or OH.

18. A composition according to claim 16, wherein the NSAIA is selected from the group consisting of: fenamic acids; indoles; and phenylalkanoic acids.

19. A composition according to claim 16, wherein the NSAIA is selected from the group consisting of:
loxoprofen; tolfenamic acid; indoprofen; pirprofen; clidanac; fenoprofen; naproxen; fenclorac; meclofenamate; benoxaprofen; carprofen; isofezolac; aceloferac; fenbufen; etodolic acid; fleclozic acid; amfenac; efenamic acid; bromfenac; ketoprofen; fenclofenac; alcofenac; orpanoxin; zomopirac; diflunisal; flufenamic acid; niflumic acid; mefenamic acid; pranoprofen; zaltoprofen; indomethacin; sulindac; tolmetin; suprofen; ketorolac; flurbiprofen; ibuprofen; and diclofenac.

20. A composition according to claim 16, wherein the NSAIA is selected from the group consisting of naproxen, flurbiprofen and diclofenac.

21. A composition according to claim 16, wherein the vehicle is a physiologically balanced irrigating solution.

22. A composition according to claim 16, wherein the compound is selected from the group consisting of:

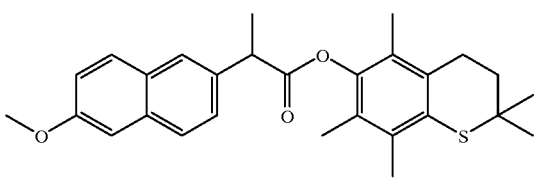

6-(1-acetyl-2,2,5,7,8-pentamethyl-3,4-dihydro-2H-benzothiin) 2-(6-methoxy-2-naphthyl)-propionate;

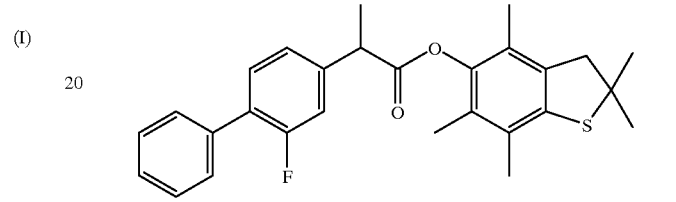

5-(1-acetyl-2,2,4,6,7-pentamethyl-2,3-dihydrobenzothiophene) 2-(3-fluoro-4-phenyl-phenyl)-propionate;

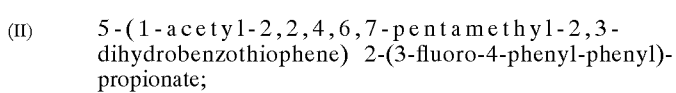

6-(1-acetyl-2-hydroxymethyl-2,5,7,8-tetramethyl-3,4-dihydro-2H-benzothiin) 2-(6-methoxy-2-naphthyl)-propionate;

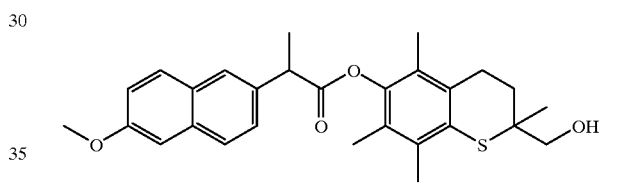

6-(1-acetyl-2-hydroxymethyl-2,5,7,8-tetramethyl-3,4-dihydro-2H-benzothiin) 2-(3-fluoro-4-phenyl-phenyl)-propionate; and

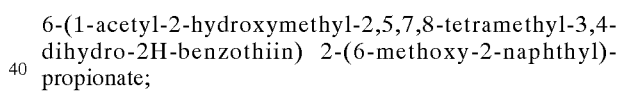

5-(1-acetyl-2-(2-hydroxyethyl)-2,4,6,7-tetramethyl-2,3-dihydrobenzothiophene) 2-(6-methoxy-2-naphthyl)-propionate.

23. A method of preventing or alleviating damage to mammalian tissues which comprises administering to a human a therapeutically effective amount of a composition comprising an amount of a compound of formula (I) or (II) effective to decrease inflammation and free radical or oxidative damage in said tissues in a pharmaceutically acceptable vehicle:

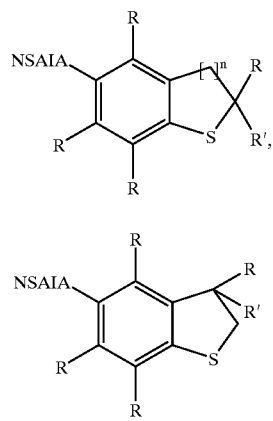

wherein:

NSAIA is a non-steroidal anti-inflammatory agent originally containing a carboxylic acid, and is attached through the acid to form a phenolic ester;

R is $C_1$–$C_3$ alkyl;

R' is $(CH_2)_m X'$;

m is 1 to 6;

X' is OH, OR, $NH_2$, NHR or H;

n is 1 to 2;

or a pharmaceutically acceptable salt thereof; and a pharmaceutically acceptable vehicle therefore.

24. The method according to claim 23, wherein the composition is administered to prevent or alleviate damage to ophthalmic tissues.

25. The method according to claim 23, wherein:

R is $CH_3$;

m is 1 to 2; and

X' is H or OH.

26. The method according to claim 23, wherein the NSAIA is selected from the group consisting of: fenamic acids; indoles; and phenylalkanoic acids.

27. The method according to claim 23, wherein the NSAIA is selected from the group consisting of:

loxoprofen; tolfenamic acid; indoprofen; pirprofen; clidanac; fenoprofen; naproxen; fenclorac; meclofenamate; benoxaprofen; carprofen; isofezolac; aceloferac; fenbufen; etodolic acid; fleclozic acid; amfenac; efenamic acid; bromfenac; ketoprofen; fenclofenac; alcofenac; orpanoxin; zomopirac; diflunisal; flufenamic acid; niflumic acid; mefenamic acid; pranoprofen; zaltoprofen; indomethacin; sulindac; tolmetin; suprofen; ketorolac; flurbiprofen; ibuprofen; and diclofenac.

28. The method according to claim 23, wherein the NSAIA is selected from the group consisting of naproxen, flurbiprofen and diclofenac.

29. The method according to claim 23, wherein the vehicle is a physiological balanced irrigating solution.

30. The method according to claim 23, wherein the compound is selected from the group consisting of:

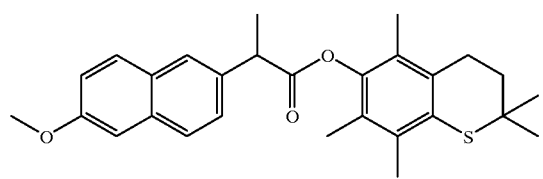

6-(1-acetyl-2,2,5,7,8-pentamethyl-3,4-dihydro-2H-benzothiin) 2-(6-methoxy-2-naphthyl)-propionate;

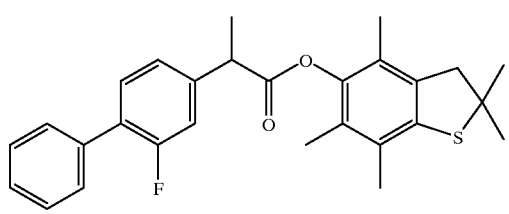

5-(1-acetyl-2,2,4,6,7-pentamethyl-2,3-dihydrobenzothiophene) 2-(3-fluoro-4-phenyl-phenyl)-propionate;

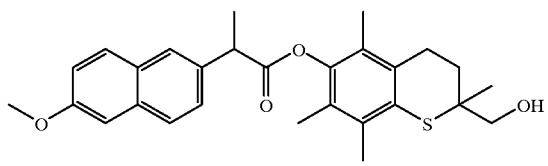

6-(1-acetyl-2-hydroxymethyl-2,5,7,8-tetramethyl-3,4-dihydro-2H-benzothiin) 2-(6-methoxy-2-naphthyl)-propionate;

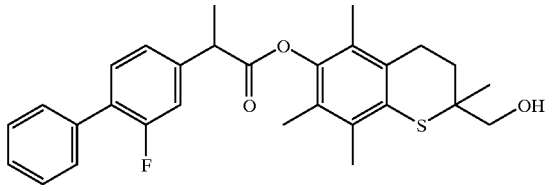

6-(1-acetyl-2-hydroxymethyl-2,5,7,8-tetramethyl-3,4-dihydro-2H-benzothiin) 2-(3-fluoro-4-phenyl-phenyl)-propionate; and

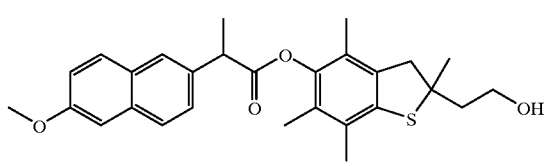

5-(1-acetyl-2-(2-hydroxyethyl)-2,4,6,7-tetramethyl-2,3-dihydrobenzothiophene) 2-(6-methoxy-2-naphthyl)-propionate.

* * * * *